United States Patent
Tamura

(10) Patent No.: US 10,506,696 B2
(45) Date of Patent: Dec. 10, 2019

(54) RADIATION IMAGING APPARATUS, RADIATION IMAGING SYSTEM, RADIATION IMAGING METHOD, AND STORAGE MEDIUM

(71) Applicant: CANON KABUSHIKI KAISHA, Tokyo (JP)

(72) Inventor: Toshikazu Tamura, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/154,888

(22) Filed: Oct. 9, 2018

(65) Prior Publication Data

US 2019/0045612 A1    Feb. 7, 2019

Related U.S. Application Data

(63) Continuation of application No. PCT/JP2017/007918, filed on Feb. 28, 2017.

(30) Foreign Application Priority Data

Apr. 28, 2016 (JP) ................. 2016-091653

(51) Int. Cl.
*G01T 1/161* (2006.01)
*H05G 1/44* (2006.01)
(Continued)

(52) U.S. Cl.
CPC ............. *H05G 1/44* (2013.01); *A61B 6/4233* (2013.01); *A61B 6/4283* (2013.01); *A61B 6/469* (2013.01); *A61B 6/50* (2013.01); *A61B 6/54* (2013.01); *A61B 6/542* (2013.01); *A61B 6/545* (2013.01); *G01T 1/247* (2013.01); *G01T 1/2928* (2013.01); *H04N 5/32* (2013.01); *H04N 5/353* (2013.01); *A61B 6/56* (2013.01)

(58) Field of Classification Search
CPC ....... G01T 1/1642; G01T 1/20; G01T 1/2006; G01T 1/2018
See application file for complete search history.

(56) References Cited

U.S. PATENT DOCUMENTS

| 7,164,115 B2 | 1/2007 | Yagi |
| 9,674,935 B2 | 6/2017 | Kuwabara et al. |

(Continued)

FOREIGN PATENT DOCUMENTS

| JP | 4217505 | 11/2008 |
| JP | 2014-090862 | 5/2014 |
| JP | 2014-090868 | 5/2014 |

*Primary Examiner* — David P Porta
*Assistant Examiner* — Mamadou Faye
(74) *Attorney, Agent, or Firm* — Venable LLP

(57) ABSTRACT

A radiation imaging system includes a detection unit configured to detect a dose of radiation irradiation from a radiation source, a first processing unit configured to output a first stop signal when dose information obtained based on first processing for a result of the detection exceeds a threshold, a second processing unit configured to output a second stop signal when dose information obtained based on second processing on a signal having undergone the first processing exceeds a threshold, and a control unit configured to control the radiation source so as to stop the radiation irradiation based on the first stop signal or the second stop signal.

19 Claims, 10 Drawing Sheets

(51) Int. Cl.
  *G01T 1/24*  (2006.01)
  *G01T 1/29*  (2006.01)
  *H04N 5/32*  (2006.01)
  *H04N 5/353*  (2011.01)
  *A61B 6/00*  (2006.01)

(56) References Cited

U.S. PATENT DOCUMENTS

| | | | |
|---|---|---|---|
| 2011/0249791 A1* | 10/2011 | Wang | A61B 6/08 378/62 |
| 2011/0317054 A1 | 12/2011 | Kameshima et al. | |
| 2013/0083892 A1* | 4/2013 | Ohta | G01T 1/2018 378/62 |
| 2013/0223592 A1* | 8/2013 | Sato | A61B 6/4233 378/62 |
| 2018/0275075 A1 | 9/2018 | Tamura et al. | |
| 2018/0292545 A1 | 10/2018 | Asai et al. | |

\* cited by examiner

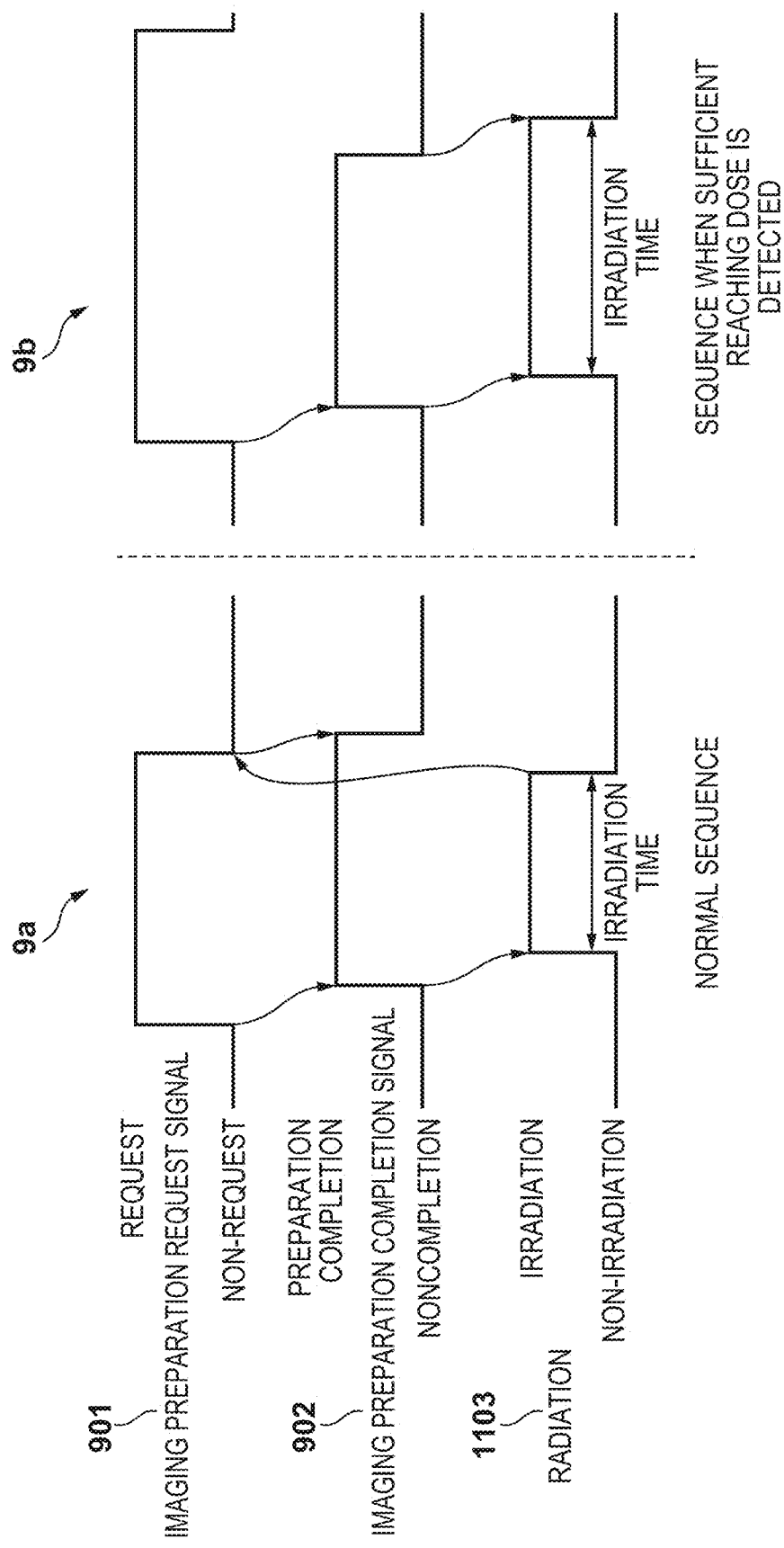

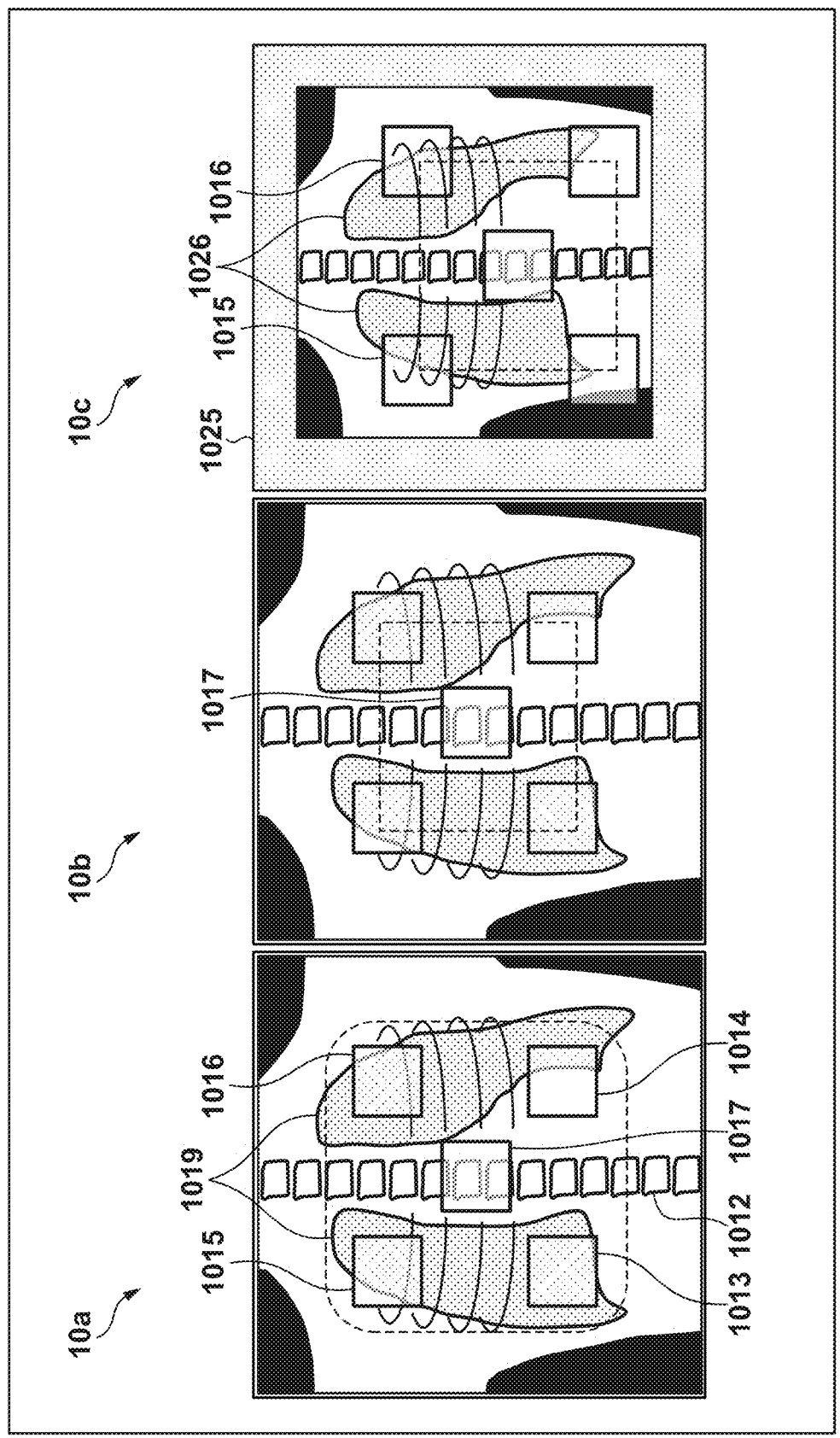

RADIATION IMAGING APPARATUS, RADIATION IMAGING SYSTEM, RADIATION IMAGING METHOD, AND STORAGE MEDIUM

CROSS-REFERENCE TO RELATED APPLICATIONS

This application is a Continuation of International Patent Application No. PCT/JP2017/007918, filed Feb. 28, 2017, which claims the benefit of Japanese Patent Application No. 2016-091653, filed Apr. 28, 2016, both of which are hereby incorporated by reference herein in their entirety.

BACKGROUND OF THE INVENTION

Field of the Invention

The present invention relates to a radiation imaging apparatus, a radiation imaging system, a radiation imaging method, and a storage medium.

Background Art

A radiation imaging apparatus including a matrix substrate including a pixel array obtained by combining switches such as TFTs (Thin Film Transistors) and conversion elements such as photoelectric conversion elements has been put into practice as a radiation imaging apparatus used for medical image diagnosis and non-destructive inspections. As an example of a multifunctional radiation imaging apparatus, PTL 1 discloses, as a radiation imaging system for performing dose control of the radiation, an arrangement in which an analog signal is input from a radiation reception portion such as a photo-timer to the dose control unit of a radiation generation apparatus, and dose control is performed such that the dose control unit stops irradiation of the radiation when an integration value of analog signals exceeds a predetermined threshold.

CITATION LIST

Patent Literature

PTL 1: Japanese Patent No. 4217505

However, when outputting dose information from a radiation imaging apparatus to a radiation generation apparatus in the form of an analog signal, the analog signal is susceptible to an influence of noise. For this reason, for example, a radiation capturing system has a problem in which precision of dose control for stopping irradiation of radiation degrades due to an influence of noise or the like when the irradiation dose from a radiation source is low.

The present invention has been made in consideration of the above problem and provides radiation imaging technique capable of performing control so as to stop irradiation of the radiation using a plurality of kinds of signals.

SUMMARY OF THE INVENTION

A radiation imaging system according to an aspect of the present invention is comprising: a detection unit configured to detect a dose of radiation irradiation from a radiation source; a first processing unit configured to output a first stop signal when dose information obtained based on first processing for a result of the detection exceeds a threshold; a second processing unit configured to output a second stop signal when dose information obtained based on second processing on a signal having undergone the first processing exceeds a threshold; and a control unit configured to control the radiation source so as to stop the radiation irradiation based on the first stop signal or the second stop signal.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 9 is a view showing the operation example of the radiation imaging system based on a digital signal; and FIG. 10 is a view showing the detection example of doses in the radiation imaging apparatus.

DESCRIPTION OF THE EMBODIMENTS

An embodiment of the present invention will be described in detail with reference to the accompanying drawings. Note that the constituent elements described in this embodiment are merely examples. The technical scope of the present invention is determined by the scope of the appended claims and is not limited by the individual embodiment to be described below. In this specification, the radiation is not limited to X-rays, but can be, for example, α-, β-, or γ-rays.

Figure 1:
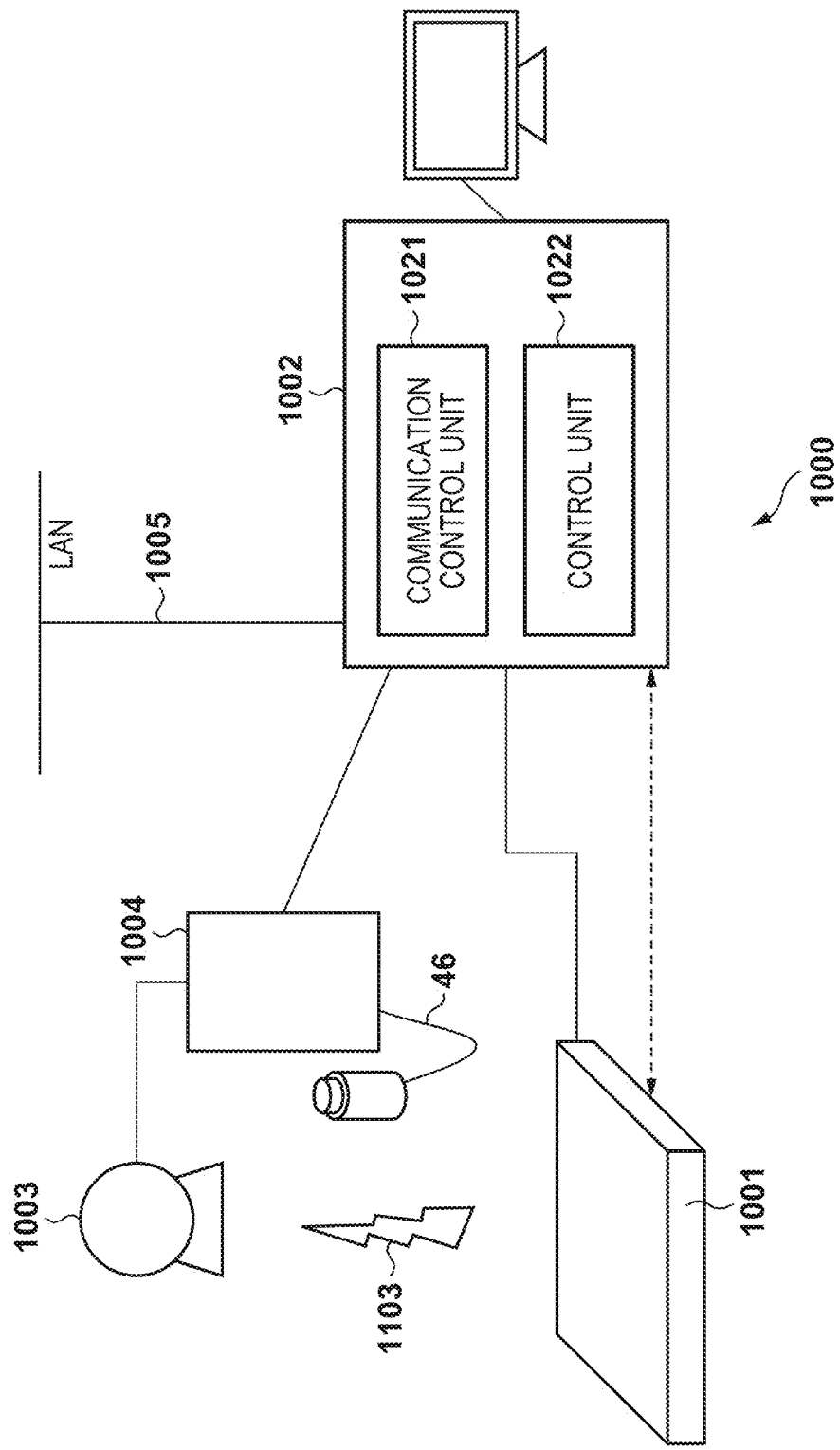
FIG. 1 is a block diagram showing an example of the arrangement of a radiation imaging system including a radiation imaging apparatus.

The arrangement and processing of a radiation imaging system 1000 according to this embodiment will be described with reference to FIG. 1. FIG. 1 is a block diagram showing an example of the arrangement of the radiation imaging system including a radiation imaging apparatus of this embodiment. The radiation imaging system is used in capturing of a radiation image in, for example, a hospital and includes, as its functional arrangements, a radiation imaging apparatus 1001, an imaging control apparatus 1002, a radiation source 1003, a high-voltage generator 1004, and a LAN 1005 (hospital LAN).

In accordance with an operation of an operation switch 46 by an operator, the radiation imaging apparatus 1001 detects radiation passing through a subject (not shown) and forms an image. The imaging control apparatus 1002 performs, for example, imaging condition settings and operation settings for the radiation imaging apparatus 1001. For example, the radiation imaging apparatus 1001 transfers an image, transmits a reaching dose, and transmits a stop signal for stopping irradiation of the radiation source 1003 to the imaging control apparatus 1002. In order to allow input and output of information such as imaging condition settings, operation settings, and image information, the imaging control apparatus 1002 holds, for example, a mouse and a keyboard as input devices and holds a display as an output device. The imaging control apparatus 1002 performs irradiation control and the like of radiation for the high-voltage generator 1004. The imaging control apparatus 1002 includes, as functional arrangements, a communication control unit 1021 for mediating communication and a control unit 1022 for performing operation settings, a dose information notification, and the like. The imaging control apparatus 1002 monitors the states of the radiation imaging apparatus 1001 and the high-voltage generator 1004 and controls radiation irradiation and imaging.

The radiation source 1003, for example, accelerates electrons with a high voltage to generate radiation and holds a radiation tube and a rotor which bombard the accelerated electrons on an anode. The subject is irradiated with radiation emitted from the radiation source 1003. The radiation imaging apparatus 1001 detects the radiation passing through the subject and forms an image.

Figure 2:
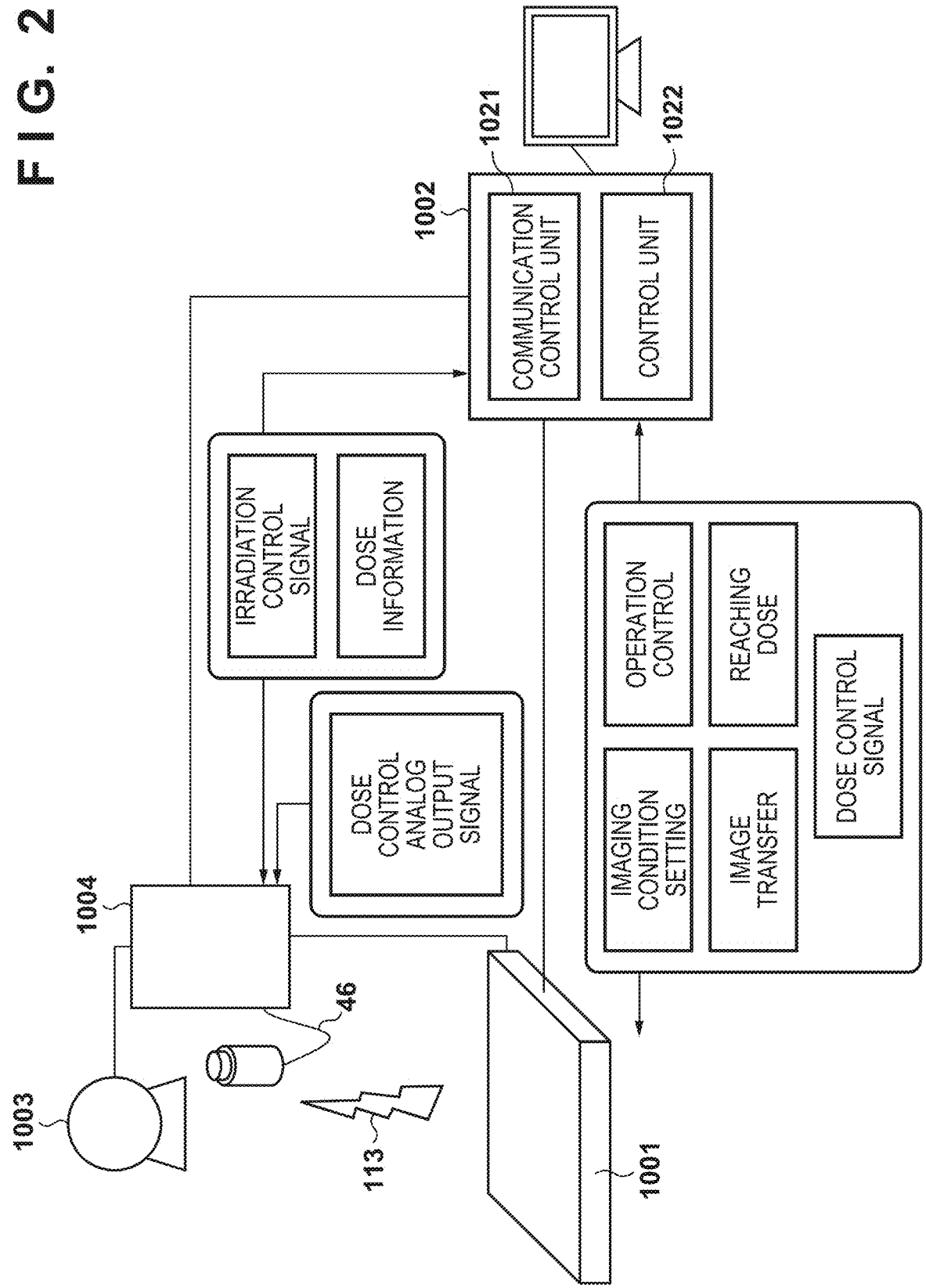
FIG. 2 is a block diagram showing an example of data communication in the radiation imaging system.

FIG. 2 is a block diagram showing the example of data communication between the imaging control apparatus 1002 and the radiation imaging apparatus 1001, data communication between the imaging control apparatus 1002 and the high-voltage generator 1004, and data communication between the radiation imaging apparatus 1001 and the high-voltage generator 1004. In communication between the imaging control apparatus 1002 and the radiation imaging apparatus 1001, information such as the imaging condition settings, the operation control settings, image transfer, the reaching dose, and the dose control signal is exchanged. In the communication between the imaging control apparatus 1002 and the high-voltage generator 1004, the dose information, the irradiation control signal, the dose control signal, and the like are exchanged.

In addition, between the radiation imaging apparatus 1001 and the high-voltage generator 1004, an analog output signal (dose control analog output signal) simulating the output of the dose control sensor is input from the radiation imaging apparatus 1001 to the high-voltage generator 1004.

The radiation imaging apparatus 1001 includes, as communication media, two communication units as a wireless communication unit and a wired communication unit, and an analog output unit. The radiation imaging apparatus 1001 can be connected to the communication control unit 1021 of the imaging control apparatus 1002 by using the two communication units. In addition, the radiation imaging apparatus 1001 can be connected to the high-voltage generator 1004 using the analog output unit. Note that the example in FIG. 2 is merely an example. The information exchanged in the communication between the imaging control apparatus 1002 and the radiation imaging apparatus 1001 and the communication between the imaging control apparatus 1002 and the high-voltage generator 1004 is not limited to the above example.

In the communication between the imaging control apparatus 1002 and the high-voltage generator 1004, dose information is an irradiation dose from the radiation source 1003. The reaching dose is a dose reaching the radiation imaging apparatus 1001, out of the irradiation doses from the radiation source 1003. In the communication between the imaging control apparatus 1002 and the radiation imaging apparatus 1001, the dose control signal is a signal including two signals, that is a stop signal for stopping the radiation irradiation and an irradiation start signal for starting the radiation irradiation.

The wired communication unit serving as the communication medium of the radiation imaging apparatus 1001 is an information transmission path and can exchange information by cable connection using a communication standard having a predetermined rule or a standard such as RS232C, USB, or an Ethernet®. The wireless communication unit serving as a communication medium of the radiation imaging apparatus 1001 is similarly an information transmission path and includes a circuit substrate having, for example, a communication IC. The wireless communication unit is electrically connected to an antenna (not shown) and exchanges radio waves. The circuit substrate including the communication IC can perform protocol communication processing based on a wireless LAN via the antenna. Note that the radio communication frequency band, standard, and method in wireless communication are not particularly limited, and short-range wireless method such as NFC (Near field radio communication) or Bluetooth®, or a UWB (Ultra Wideband) method may be used. In addition, the wireless communication unit has a plurality of wireless communication methods, and an appropriate method may be selected from the plurality of wireless communication method and perform communication.

Figure 3:
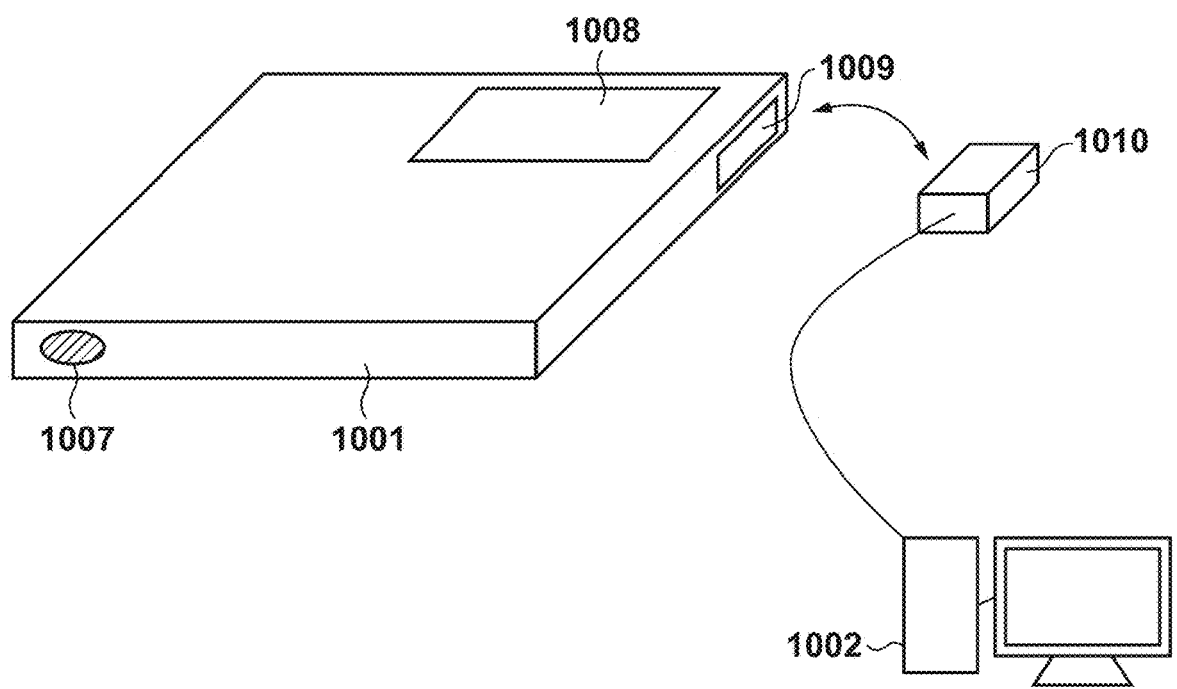
FIG. 3 is a view exemplifying the external arrangement of the radiation imaging apparatus.

The radiation imaging apparatus 1001 can be arranged as, for example, a portable cassette flat panel detector (FPD (Flat Panel Detector)). FIG. 3 is a view exemplifying the outer arrangement of the portable radiation imaging apparatus 1001. The radiation imaging apparatus 1001 includes a power button 1007 for turning on/off the power supply, a battery unit 1008 for supplying the power, and a connector connection unit 1009. The battery unit 1008 is arranged to be detachable. The battery main body of the battery unit 1008 is chargeable by a battery charger.

The radiation imaging apparatus 1001 is connectable to the imaging control apparatus 1002 using a sensor cable 1010. The radiation imaging apparatus 1001 is connectable to the sensor cable 1010 via the connector connection unit 1009. When the radiation imaging apparatus 1001 and the imaging control apparatus 1002 are connected via the sensor cable 1010, this connection is switched to communication using the wired communication unit. The information communication between the radiation imaging apparatus 1001 and the imaging control apparatus 1002 shown in FIG. 2 is performed by the wired communication. Regardless of a communication form, the imaging control apparatus 1002 can control the communication unit such that the communication unit can be switched in accordance with a user operation.

Figure 4:
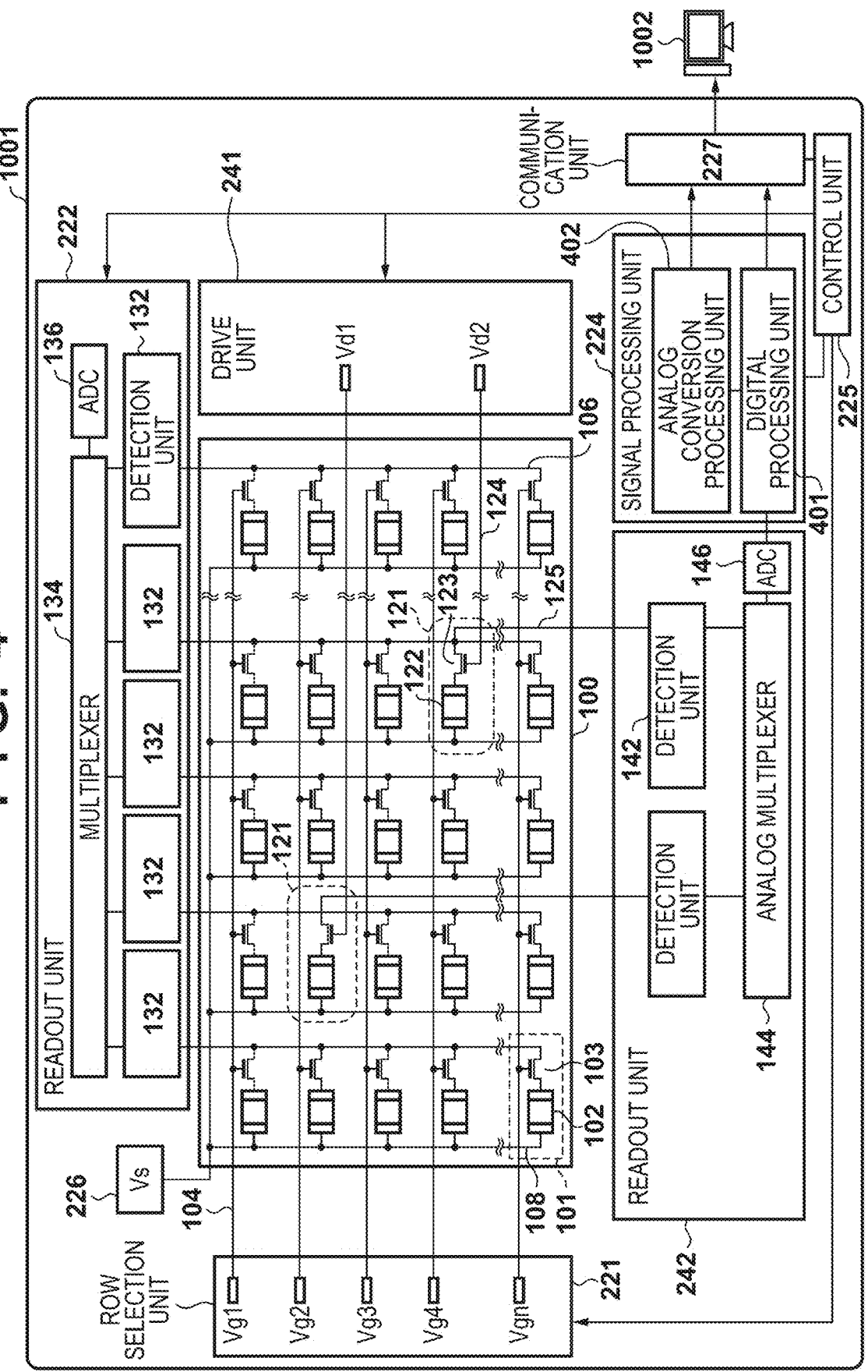
FIG. 4 is a block diagram exemplifying the internal arrangement of the radiation imaging apparatus.

FIG. 4 is a block diagram showing the internal arrangement example of the radiation imaging apparatus 1001 according to this embodiment. The radiation imaging apparatus 1001 includes a plurality of pixels arrayed in an imaging region 100 so as to form a plurality of rows and a plurality of columns. The plurality of pixels comprise a plurality of imaging pixels 101 for detecting radiation and obtaining a radiation image based on the detected radiation, and dose detection pixels 121 (detection units) for detecting the dose of radiation emitted from the radiation source. Each imaging pixel 101 includes a first conversion element 102 for converting radiation into an electrical signal, and a first switch 103 arranged between a corresponding column signal line 106 and the corresponding first conversion element 102. Each dose detection pixel 121 includes a second conversion element 122 for converting radiation into an electrical signal and a second switch 123 arranged between a corresponding detection signal line 125 and the corresponding second conversion element 122.

Each of the first conversion element 102 and the second conversion element 122 can be formed from a scintillator for converting radiation into light and a photoelectric conversion element for converting the light into an electrical signal. The scintillator is generally made in the form of a sheet so as to cover the imaging region 100 and can be shared by the plurality of pixels. Alternatively, each of the first conversion element 102 and the second conversion element 122 is formed from a conversion element for directly converting radiation into light.

Each of the first switch 103 and the second switch 123 can include a thin film transistor (TFT) in which an active region is formed by a semiconductor such as amorphous silicon or polysilicon (preferably polysilicon).

The radiation imaging apparatus 1001 includes a plurality of column signal lines 106 and a plurality of drive lines 104. Each column signal line 106 corresponds to one of the plurality of columns in the imaging region 100. Each drive line 104 corresponds to one of the plurality of rows in the imaging region 100. A row selection unit 221 (drive unit) supplies a drive signal to the each drive line 104 to drive the drive line.

The first electrode of the first conversion element 102 is connected to the first main electrode of the first switch 103, and the second electrode of the first conversion element 102 is connected to a corresponding bias line 108. One bias line 108 extends in the column direction and is commonly connected to the second electrodes of the plurality of first conversion element 102 arrayed in the column direction. The bias line 108 receives a bias voltage Vs from a power supply unit 226. The second main electrodes of the first switches 103 of the plurality of imaging pixels 101 forming one column are connected to one column signal line 106. The control electrodes of the first switches 103 of the plurality of imaging pixels 101 forming one row are connected to one drive line 104.

The plurality of column signal lines 106 are connected to a readout unit 222. In this case, the readout unit 222 can include a plurality of detection units 132, a multiplexer 134, and an analog-to-digital converter (to be referred to as an AD converter hereinafter) 136. Each of the plurality of column signal lines 106 is connected to a corresponding one of the plurality of detection units 132 of the readout unit 222. One column signal line 106 corresponds to one detection unit 132. The detection unit 132 includes, for example, a differential amplifier. The multiplexer 134 sequentially selects the plurality of detection units 132 in a predetermined order and supplies a signal from the selected detection unit 132 to the AD converter 136. The AD converter 136 converts the supplied analog signal into a digital signal and outputs the digital signal.

The first electrode of each second conversion element 122 is connected to the first main electrode of the corresponding second switch 123, and the second electrode of each second conversion element 122 is connected to the corresponding bias line 108. The second main electrode of each second switch 123 is electrically connected to the corresponding detection signal line 125. The control electrode of each second switch 123 is electrically connected to the corresponding drive line 124. The radiation imaging apparatus 1001 can include the plurality of detection signal lines 125. One detection signal line 125 can be connected to one or the plurality of dose detection pixels 121. The drive line 124 is driven by a drive unit 241. One or the plurality of dose detection pixels 121 can be connected to one drive line 124.

The detection signal line 125 is connected to a readout unit 242 (AEC sensor readout unit). In this case, the readout unit 242 (AEC sensor readout unit) can include a plurality of detection units 142, a multiplexer 144, and an AD converter 146. Each of the plurality of detection signal lines 125 can be connected to the corresponding one of the plurality of detection units 142 of the readout unit 242. One detection signal line 125 corresponds to one detection unit 142. The detection unit 142 includes, for example, a differential amplifier. The multiplexer 144 sequentially selects the plurality of detection units 142 in a predetermined order and supplies a signal from the selected detection unit 142 to the AD converter 146. The AD converter 146 converts the supplied analog signal into a digital signal and outputs the digital signal.

The output from the AD converter 146 of the readout unit 242 (AEC sensor readout unit) is supplied to a signal processing unit 224 and processed by the signal processing unit 224. Based on the output from the AD converter 146 of the readout unit 242, the signal processing unit 224 outputs information indicating radiation irradiation for the radiation imaging apparatus 1001. The signal processing unit 224 of the radiation imaging apparatus 1001 according to this embodiment includes a digital processing unit 401 for outputting a stop signal when the dose information obtained based on the first processing (digital signal processing) on the detection result of the dose detection pixel 121 (detection unit) exceeds a threshold, and an analog conversion processing unit 402 (conversion processing unit) for outputting a signal having undergone the second processing (analog conversion processing) on the signal having undergone the first processing (digital signal processing) by the digital processing unit 401.

As the first processing, the digital processing unit 401 (first processing unit) generates a signal obtained by performing digital signal processing on the detection result of the dose detection pixel 121 (detection unit). The digital processing unit 401 (first processing unit) can output the generated signal as a synchronization control signal with the radiation source 1003. The digital processing unit 401 (first processing unit) is arranged, for example, to detect radiation irradiation for the radiation imaging apparatus 1001 and calculate the radiation irradiation dose and the integrated irradiation amount (integration dose) based on the generated signal. The digital processing unit 401 (first processing unit) can output a stop signal (first stop signal) when the dose information obtained based on the first processing (digital signal processing) on the detection result by the dose detection pixel 121 (detection unit) exceeds a threshold. In order to perform use for the radiation dose detection application, the second conversion element 122 of the dose detection pixel 121 can be arranged for the number of elements equal to or less than, for example, several % for the first conversion elements 102 forming the imaging pixels for obtaining a radiation image. In addition, in order to cause the second conversion elements 122 to cope with various kinds of measurements so as to image a variety of imaging portions, the second conversion elements 122 can be arranged to be distributed on the entire surface of the imaging region 100. The distribution of the second conversion elements 122 can be formed such that the second conversion elements 122 are uniformly distributed within the plane of the imaging region 100, the second conversion elements 122 are distributed on the central portion of the imaging region 100 in which the region of interest is concentrated, or the second conversion elements 122 are distributed to increase the density of the peripheral portion of the imaging region 100 in order to use them for irradiation area detection or the like.

As the second processing, the analog conversion processing unit 402 (conversion processing unit) generates a signal obtained by performing analog conversion processing on a signal generated by the digital processing unit 401 (first processing unit). The analog conversion processing unit 402 (conversion processing unit) performs analog conversion of the irradiation dose calculated by the digital processing unit 401, generates an analog output signal (dose control analog output signal) simulating the output of the dose control sensor, and outputs the analog output signal. That is, the analog conversion processing unit 402 (conversion processing unit) can output a signal having undertone the second processing (analog conversion processing) on the signal having undergone the first processing (digital signal processing) by the digital processing unit 401 (first processing unit).

A control unit 225 controls the row selection unit 221, the drive unit 241, and the readout unit 242 based on the information from the signal processing unit 224. The control unit 225 controls, for example, the start and end of storage of charges corresponding to the radiation entering the imaging pixels 101 based on the information from the signal processing unit 224. The radiation imaging apparatus 1001 includes a communication unit 227 for performing communication with the imaging control apparatus 1002. The communication unit 227 includes two communication units as a wired communication unit and a wireless communication unit for outputting signals via the digital signal path (first signal path), and an analog output unit for outputting an analog output signal (dose control analog output signal) simulating the output of the dose control sensor via the analog signal path (second signal path). That is, the communication unit 227 outputs the signal output from the digital processing unit 401 (first processing unit) via the digital signal path (first signal path) and outputs, via the analog signal path (second signal path), the signal output from the analog conversion processing unit 402 (conversion processing unit).

The arrangement of the radiation imaging system 1000 according to this embodiment will be described with reference to FIG. 5. A signal from the radiation source 1003 and a signal from an operation signal processing unit 1041 are input to the radiation generation control unit 1042 of the high-voltage generator 1004. A signal indicating the stable state of anode rotation and a signal indicating the temperature state are input from the radiation source 1003 to a radiation generation control unit 1042. The operation switch 46 is connected to the operation signal processing unit 1041, and an input signal of the switch operation of the operator is input to the radiation generation control unit 1042.

Signals about the exposure states are input from the radiation imaging apparatus 1001 and the imaging control apparatus 1002 to the radiation generation control unit 1042 via a signal selection unit 1043, a signal integration determination unit 1044, or a signal processing unit 1045.

The analog conversion processing unit 402 (conversion processing unit) and the signal integration determination unit 1044 (integration determination unit) form the second processing unit in the radiation imaging system 1000 of this embodiment. The second processing unit outputs a stop signal (second stop signal) when the dose information obtained based on the second processing (analog conversion processing) for a signal having undergone the first processing (digital signal processing) by the digital processing unit 401 (first processing unit) exceeds a threshold. In this case, the analog conversion processing unit 402 (conversion processing unit) outputs a signal obtained by performing the second processing (analog conversion processing) on the signal having undergone the first processing (digital signal processing) by the digital processing unit 401 (first processing unit). The signal integration determination unit 1044 determines whether the dose information obtained by performing integration of the signal output from the analog conversion processing unit 402 (conversion processing unit) exceeds a threshold. If the signal integration determination unit 1044 (integration determination unit) determines that the dose information exceeds the threshold, the second processing unit outputs a stop signal (second stop signal).

The radiation generation control unit 1042 controls the radiation source 1003 based on the second stop signal output from the digital processing unit 401 (first processing unit) or the second processing unit. That is, the radiation generation control unit 1042 controls the radiation source 1003 to stop radiation irradiation based on the first stop signal or the second stop signal.

The signal selection unit 1043 (selection unit) receives the stop signal (second stop signal) of radiation 1103 input from the signal integration determination unit 1044 (integration determination unit) via the analog signal path (second signal path) and the stop signal (first stop signal) of the radiation 1103 input from the signal processing unit 1045 via the digital signal path (first signal path). The signal selection unit 1043 (selection unit) selects the first input stop signal, and the selected stop signal is transmitted to the radiation generation control unit 1042. That is, the signal selection unit 1043 (selection unit) selects the input first stop signal or the input second stop signal. At this time, the signal selection unit 1043 (selection unit) selects the first input signal to the signal selection unit 1043 (selection unit) out of the first stop signal and the second stop signal.

The radiation generation control unit 1042 performs radiation generation control while confirming input states. The radiation generation control unit 1042 performs irradiation control of radiation from the radiation source 1003 based on an input exposure state signal. That is, the radiation generation control unit 1042 controls the radiation source 1003 so as to stop radiation irradiation based on the signal selected by the signal selection unit 1043 (selection unit).

The radiation imaging apparatus 1001 can communicate with the signal processing unit 1045 of the high-voltage generator 1004 via a relay unit 1023 and a signal processing unit 1024 of the imaging control apparatus 1002. A signal indicating the imaging preparation state is input from the radiation imaging apparatus 1001 to the signal processing unit 1045 via the relay unit 1023 and the signal processing unit 1024 of the imaging control apparatus 1002. The signal processing unit 1045 inputs the input signal indicating the imaging preparation state to the radiation generation control unit 1042. When the communication between the radiation imaging apparatus 1001 and the imaging control apparatus 1002 is wireless communication, the relay unit 1023 functions as an access point. If the communication is wired communication, the relay unit 1023 serves as a switching hub. The communication control unit 1021 is further connected to the relay unit 1023, and the function of the communication control unit 1021 is implemented by application software operating on a platform such as a PC (information processing apparatus).

This embodiment has signal paths for two kinds of dose control by an analog signal and a digital signal. One signal path is an analog signal path (second signal path) for dose control and is connected from the communication unit 227 of the radiation imaging apparatus 1001 to the signal integration determination unit 1044 of the high-voltage generator 1004. This analog signal is an output signal (dose control analog output signal) simulating the output from a dose control sensor 1011. Since a processing circuit of the high-voltage generator 1004 for processing the analog output signal of the dose control sensor 1011 can be used, this connection form is a connection form in which the processing of the high-voltage generator 1004 need not be changed. Note that the dose control sensor 1011 is a dose control sensor using an ion chamber method, a method for applying a phosphor to an optical fiber and detecting the dose using an image intensifier, or a method using a thin film semiconductor sensor. As will be described later, this signal path has an arrangement in which the dose control circuit arrangement is included in the high-voltage generator 1004.

Figure 5:
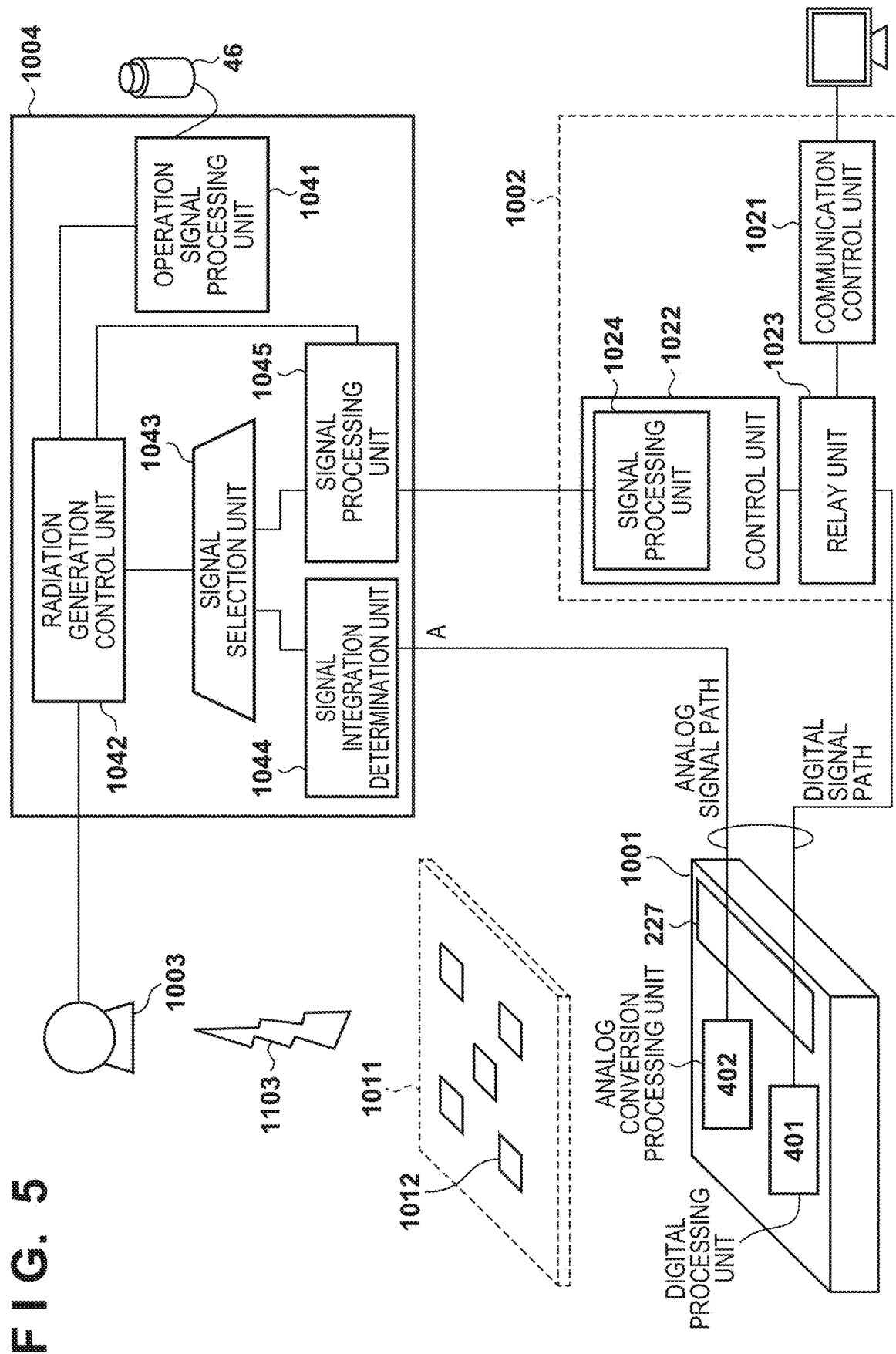
FIG. 5 is a block diagram exemplifying the arrangement of the radiation imaging system.

As shown in FIG. 5, five lighting fields 1012 are set in the dose control sensor 1011. Note that the setting of the lighting fields 1012 is merely an example, and the scope of this embodiment is not limited to this. In the example of FIG. 5, the lighting fields 1012 corresponding to the five areas respectively correspond to the plurality of dose detection pixels 121 of the radiation imaging apparatus 1001. The operator can select the lighting field 1012 from the predetermined irradiation area patterns on a user interface (setting unit) (not shown) on the high-voltage generator 1004. Based on an operation input of the operator, the user interface (setting unit) sets an irradiation area of the radiation source. When the irradiation area of the radiation source is set, the control unit 225 (identifying unit) of the radiation imaging apparatus 1001 can identify the dose detection pixel 121 (detection unit) arrayed at a position corresponding to the set irradiation area out of the plurality of dose detection pixels 121 (detection unit) arrayed in the imaging region 100. The control unit 1022 (obtaining unit) of the imaging control apparatus 1002 can obtain information of the imaging portion of the subject in accordance with information of an imaging order system such as an HIS (Hospital Information System)/RIS (Radiology Information System) via the LAN 1005. When the information of the imaging portion of the subject is obtained by the control unit 1022 (obtaining unit), the control unit 225 (identifying unit) of the radiation imaging apparatus 1001 can identify the dose detection pixel 121 (detection unit) arrayed at the position corresponding to the imaging portion of the subject out of the plurality of dose detection pixels 121 (detection units) arrayed in the imaging region 100. The digital processing unit 401 (first processing unit) of the radiation imaging apparatus 1001 obtains the dose information based on the detection result of the identified dose detection pixel 121 (detection unit). At the position corresponding to each lighting field, the analog conversion processing unit 402 (conversion processing unit) of the radiation imaging apparatus 1001 generates an analog output signal (dose control analog output signal (stop signal (second stop signal))) simulating the output of the dose control sensor and outputs the analog output signal.

The normal operation example of the radiation imaging system 1000 based on a signal input from the analog signal path will be described with reference to FIGS. 6 and 7a of FIG. 7. There can be a merit by which a higher-speed response can be performed for the irradiation of the radiation 1103 by an arrangement and operation (to be described later) in the analog signal path. To the contrary, since the signal is the analog signal, it is susceptible to the influence of circuit noise and an error and the influence of external noise.

Upon irradiation with the radiation 1103, signal charges by the radiation are generated in the dose detection pixel 121. The charges stored in the dose detection pixel 121 are converted into a digital signal by the AD converter 146 (ADC) in FIG. 6. In the digital processing unit 401 (first processing unit), the AD-converted dose information is weighted and added with the output value of the dose detection pixel 121 present in each lighting field 1012 for each predetermined time. The weighted and added dose information undergoes DA conversion processing (analog conversion processing) in the analog conversion processing unit 402 (conversion processing unit), and is output. An analog current 701 is output as the dose control analog output signal (stop signal (second stop signal)) for every five lighting fields 1012 (point A in each of FIGS. 5 and 6).

Figure 6:
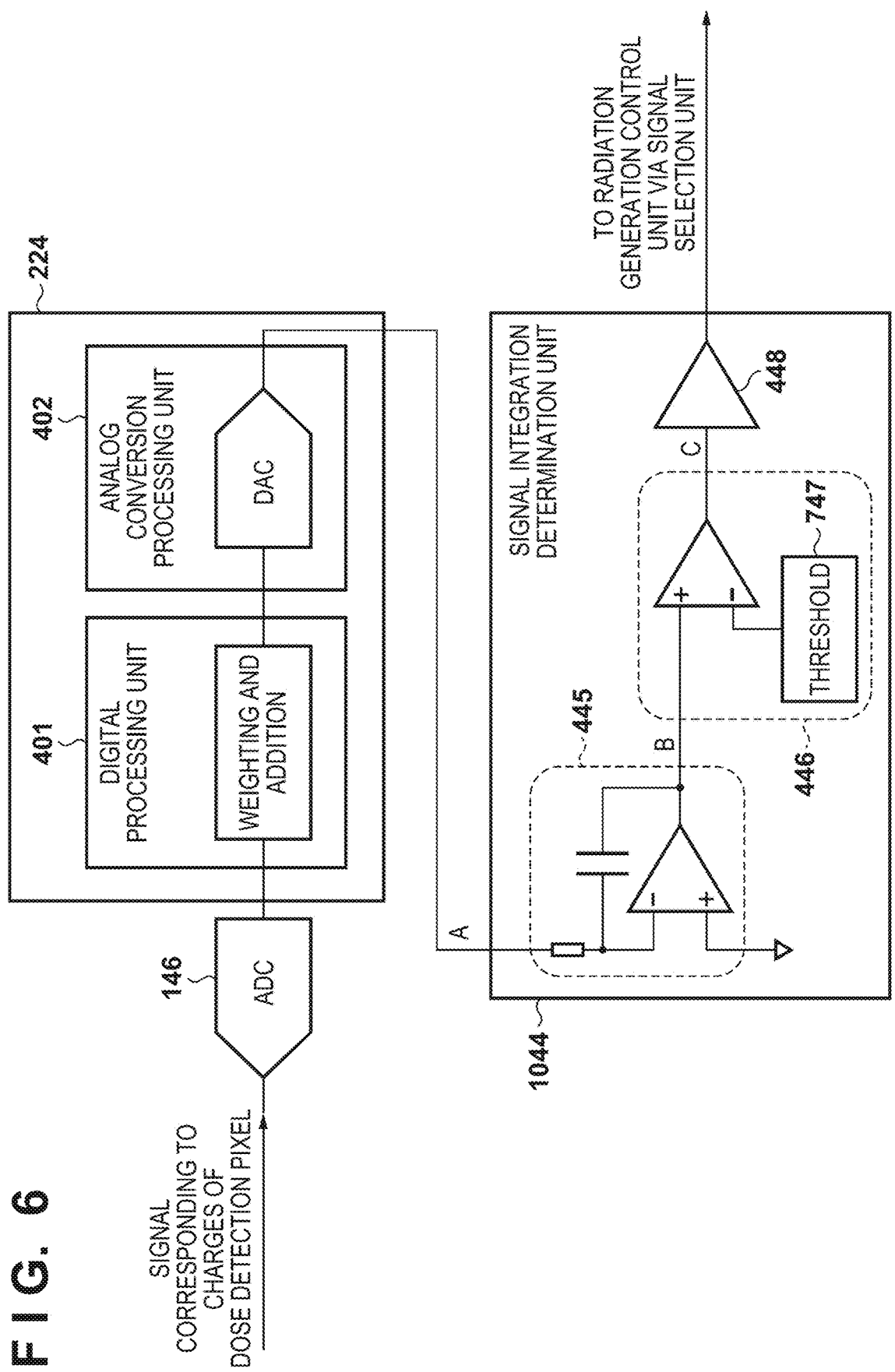
FIG. 6 is a block diagram exemplifying the arrangement of analog signal processing.
Figure 7:
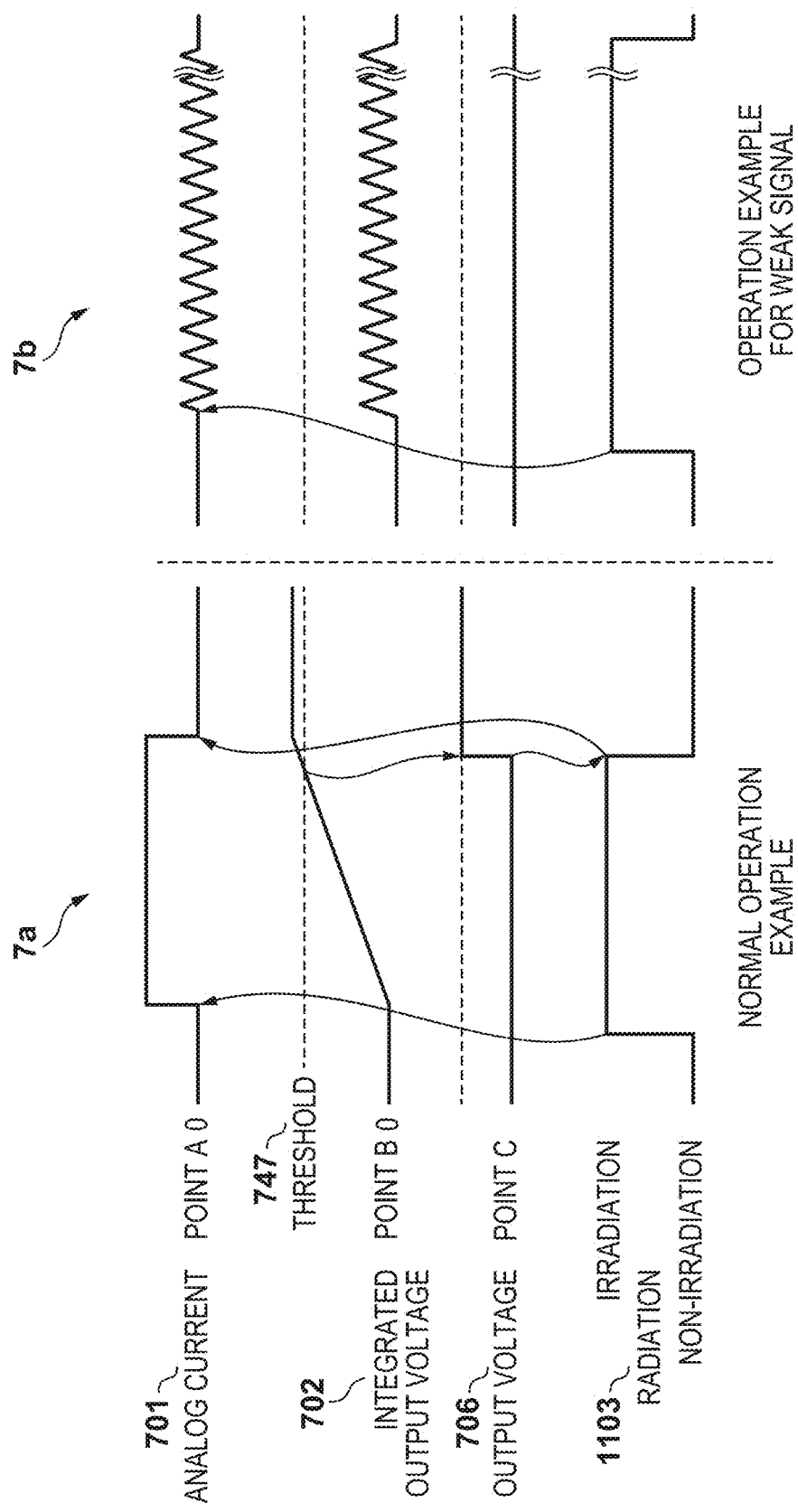
FIG. 7 is a view showing the operation example of the radiation imaging system based on an analog signal.

FIG. 6 explains the sequence of signal processing of one system, but the signal processing unit 224 can process outputs of five systems corresponding to the five lighting fields 1012. Alternatively, based on subject imaging portion information obtained from a selection result on the user interface (setting unit) on the high-voltage generator 1004 and information of an imaging order system such as an HIS/RIS, the signal processing unit 224 can selectively output a necessary dose control analog output signal (stop signal (second stop signal)) corresponding to a lighting field out of the five lighting fields 1012. The signal integration determination unit 1044 of the high-voltage generator 1004 performs processing of a signal output from the signal processing unit 224. A signal integration unit 445 of the signal integration determination unit 1044 integrates the input analog current 701 (analog current at point A in FIG. 6) and outputs the integrated analog current. In the analog current integrated by the signal integration unit 445, the output voltage (absolute value) is gradually increased like a waveform of an integrated output voltage 702 (7a in FIG. 7). The integrated output voltage 702 indicates an output voltage at point B in FIG. 6.

A determination unit 446 of the signal integration determination unit 1044 performs comparison determination processing for comparing a threshold 747 with the analog current integrated by the signal integration unit 445. When the integrated output voltage 702 exceeds the threshold 747, an output voltage 706 from the determination unit 446 changes (voltage at point C in FIG. 6). By changing the output from the determination unit 446, the determination unit 446 determines that the integrated dose of the radiation 1103 reaches a predetermined dose. An amplification unit 448 of the signal integration determination unit 1044 converts the level of the change in output voltage from the determination unit 446 into an appropriate level and outputs the appropriate level. The output signal from the signal integration determination unit 1044 is transmitted to the radiation generation control unit 1042 via the signal selection unit 1043. Based on the output signal from the signal selection unit 1043, the radiation generation control unit 1042 controls the radiation source 1003 to stop the irradiation of the radiation 1103 and stops the radiation irradiation. The radiation 1103 is changed from the irradiation state to the non-irradiation state based on the control of the radiation generation control unit 1042. When the radiation 1103 is set from the irradiation state to the non-irradiation state, the analog current 701 (analog current at point A in FIG. 6) changes to zero.

An operation example of the radiation imaging system 1000 when the radiation reaching dose is very low will be described with reference to 7b in FIG. 7. If the radiation reaching the dose detection pixel 121 per unit time is small, a signal detected by the dose detection pixel 121 is very weak. As in 7a of FIG. 7, the analog current 701 is output (point A of each of FIGS. 5 and 6) as the dose control analog output signal (stop signal (second stop signal)) for each of the five lighting fields 1012. In a case of 7b of FIG. 7, since the radiation dose is very low, the waveform of the analog current 701 is enlarged in the vertical direction and displayed. As shown in the enlarged waveform of the analog current 701 shown in 7b of FIG. 7, the analog current output may not be stabilized due to system noise, an analog circuit offset, external electromagnetic noise, or the like. This phenomenon tends to occur when the signal path of the weak analog signal is longer. In this case, the integrated output voltage 702 (point B) does not exhibit an increasing tendency unlike 7a of FIG. 7. The integrated output voltage 702 (point B) may not reach the threshold regardless of the state in which irradiation state of the radiation 1103 continues.

In this case, based on the dose control analog output signal (stop signal (second stop signal)) input from the analog signal path (second signal path) to the signal integration determination unit 1044 of the high-voltage generator 1004, the radiation generation control unit 1042 cannot control to stop the radiation irradiation. In the radiation imaging system 1000 of this embodiment, even if the irradiation stop cannot be controlled based on the analog signal, the radiation generation control unit 1042 can control to stop the radiation irradiation based on the signal input from the dose control digital signal path. Alternatively, the radiation generation control unit 1042 can control to stop the radiation irradiation in accordance with the timeout time set by the radiation time setting on a user interface (not shown) in the high-voltage generator 1004.

Note that in FIG. 5, the analog signal path (second signal path) is connected from the radiation imaging apparatus 1001 to the high-voltage generator 1004. However, the signal path may be designed via the imaging control apparatus 1002 like the digital signal path. Alternatively, the analog conversion processing unit 402 of the radiation imaging apparatus 1001 may be arranged in the imaging control apparatus 1002. In this embodiment, in order to use the signal path for dose control, the signal path is arranged such that the signal for controlling to stop the radiation irradiation can be transmitted in, for example, several ms. From this viewpoint, it is possible to arrange the analog signal path by a wired connection. In addition, by confirmation or prediction control of a signal path, the reliability and responsiveness are ensured to form the analog signal path using wireless communication.

Next, a digital signal path (first signal path) for dose control will be described below. This signal path can be obtained by using a dedicated digital signal path for transmitting an imaging preparation handshake signal between the high-voltage generator 1004 and the radiation imaging apparatus 1001 or an equivalent signal path and circuit. The handshake operation at the time of radiation imaging will be described with reference to FIGS. 8 and 9.

In a normal operation sequence shown in 9a of FIG. 9, by an operation of the operation switch 46 by the operator, the radiation generation control unit 1042 performs preparation for radiation generation. When stability of an anode rotation speed of the radiation source 1003 and preparation for other internal circuits are completed, the signal processing unit 1045 of the high-voltage generator 1004 outputs an imaging preparation request signal 901 as a request level signal based on a signal input from the radiation generation control unit 1042 (9a of each of FIGS. 8 and 9).

The imaging preparation request signal 901 (request level) output from the signal processing unit 1045 of the high-voltage generator 1004 is transmitted to the radiation imaging apparatus 1001 via the signal processing unit 1024 of the imaging control apparatus 1002. After that, when the imaging preparation is completed, the radiation imaging apparatus 1001 outputs a signal indicating the imaging preparation completion. Based on the signal input from the radiation imaging apparatus 1001, the signal processing unit 1024 of the imaging control apparatus 1002 outputs a signal indicating that an imaging preparation completion signal 902 is set at the preparation completion level (9a in FIG. 9). The imaging preparation completion signal 902 (preparation completion level) is input to the radiation generation control unit 1042 via the signal processing unit 1045 of the high-voltage generator 1004. In this case, the imaging preparation completion signal output from the radiation imaging apparatus 1001 corresponds to an irradiation start signal for starting radiation irradiation. The radiation generation control unit 1042 monitors the states of other signals and performs irradiation of the radiation 1103 upon confirmation that these signals are set in the preparation states. In this case, the radiation generation control unit 1042 can control to stop the radiation irradiation based on the radiation irradiation time set by the operator. The radiation 1103 is changed from the irradiation state to the non-irradiation state based on control (irradiation stop control) of the radiation generation control unit 1042 (9a in FIG. 9).

Based on the signal input from the radiation generation control unit 1042, the signal processing unit 1045 of the high-voltage generator 1004 changes the level of the imaging preparation request signal 901 to a non-request level and outputs it (non-request output). That is, based on the signal input from the radiation generation control unit 1042, the signal processing unit 1045 outputs a signal (imaging preparation request signal 901 (non-request level)) obtained by changing the imaging preparation request signal 901 to the non-request level. The imaging preparation request signal 901 (non-request level) output from the signal processing unit 1045 of the high-voltage generator 1004 is transmitted to the radiation imaging apparatus 1001 via the signal processing unit 1024 of the imaging control apparatus 1002. In response to the signal of the imaging preparation request signal 901 (non-request level), the radiation imaging apparatus 1001 changes the state of the radiation imaging apparatus 1001 from the imaging preparation completion state to the preparation noncompletion state.

Figure 8:
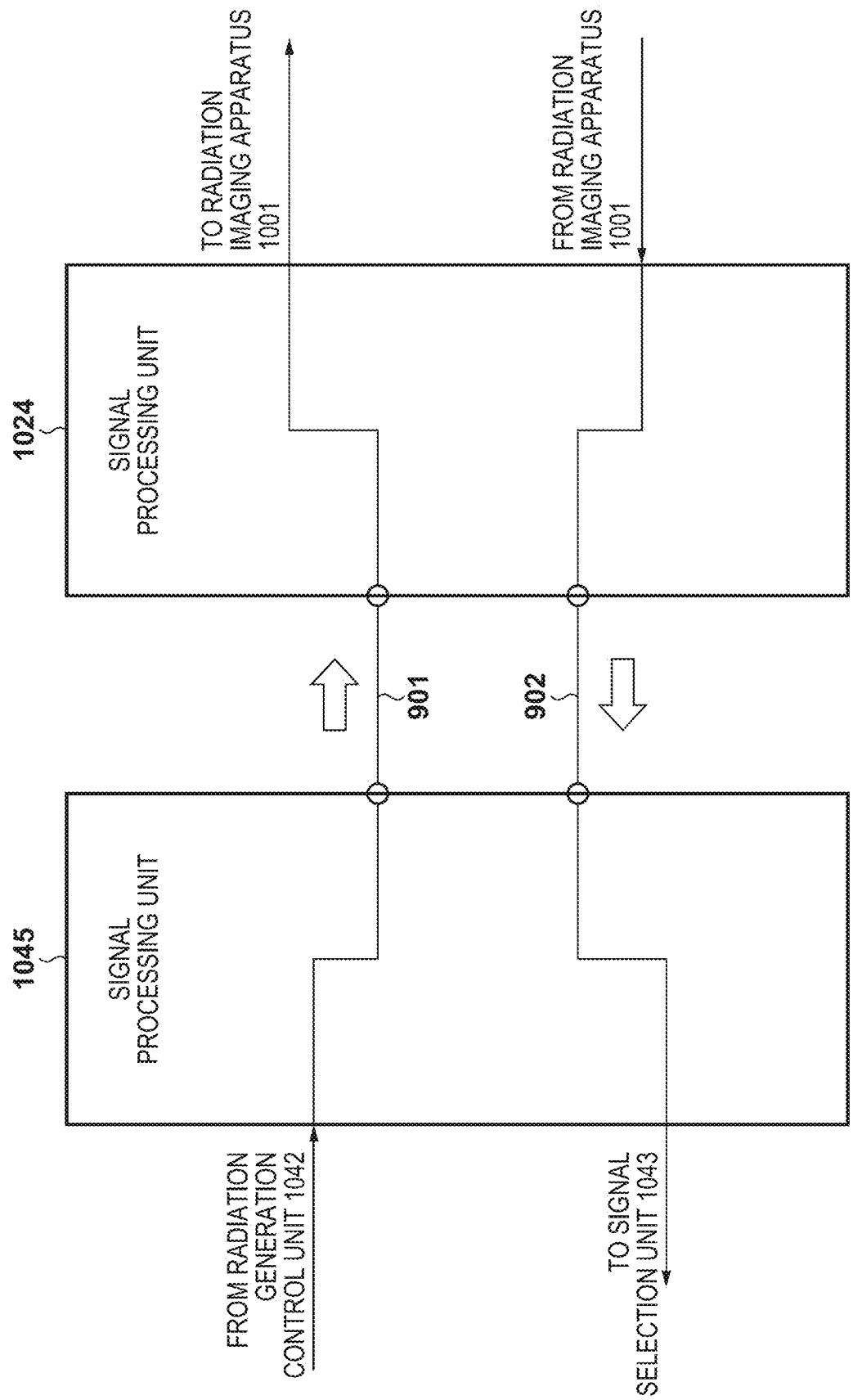
FIG. 8 is a block diagram exemplifying the arrangement of a signal generation unit of a digital signal path.

An operation sequence when a sufficient reaching dose is detected before an elapse of the set radiation irradiation time will be described with reference to 9b in FIG. 9. The operation until the actual irradiation of the radiation 1103 is the same as the operation sequence in 9a of FIG. 9. After that, when a sufficient reaching dose is detected in the radiation imaging apparatus 1001 by a method to be described later, the signal processing unit 1024 outputs, based on the signal output from the radiation imaging apparatus 1001, a signal indicating that the imaging preparation completion signal 902 is changed from the preparation completion level to the preparation noncompletion level (noncompletion level) even if the imaging preparation request signal 901 is set in the state of the request level. If the sufficient reaching dose is detected in the radiation imaging apparatus 1001, the signal output from the radiation imaging apparatus 1001 corresponds to a stop signal (first stop signal) output from the digital processing unit 401 (first processing unit) when the dose information obtained based on the first processing (digital signal processing) exceeds the threshold. In the case shown in 9b of FIG. 9, when the sufficient reaching dose is detected in the radiation imaging apparatus 1001, the preparation completion level is changed to the state (noncompletion state) of the preparation noncompletion level before the elapse of the set radiation irradiation time. The imaging preparation completion signal 902 (noncompletion level) is input from the signal processing unit 1024 to the signal processing unit 1045 of the high-voltage generator 1004. If the imaging preparation request signal 901 is set in the state of the request level and the imaging preparation completion signal 902 is set in the state of the noncompletion level, the signal processing unit 1045 outputs, to the signal selection unit 1043, the imaging preparation completion signal 902 (noncompletion state) input from the signal processing unit 1024 as the stop signal of the radiation 1103 in the digital signal path (FIG. 8). That is, the stop signal (first stop signal) output from the digital processing unit 401 (first processing unit) is input to the signal selection unit 1043 via the relay unit 1023 and the signal processing unit 1024 of the imaging control apparatus 1002 and the signal processing unit 1045 of the high-voltage generator 1004.

In the case of 9b in FIG. 9, for example, if the stop signal (first stop signal) output from the digital processing unit 401 (first processing unit) is input to the signal selection unit 1043 prior to the stop signal (second stop signal) input via the analog signal path (second signal path), the radiation generation control unit 1042 detects that the imaging preparation completion signal 902 has been changed from the preparation completion state to the preparation noncompletion state based on the stop signal (first stop signal) input first to the signal selection unit 1043. That is, the radiation generation control unit 1042 detects that the dose information (integration dose) has reached a predetermined dose and controls the radiation source 1003 so as to stop irradiation of the radiation 1103.

Note that in FIG. 9, signals are expressed in the logical circuit signal format. However, as for the imaging preparation request signal 901 and the imaging preparation completion signal 902, communication between the high-voltage generator 1004 and the radiation imaging apparatus 1001 can be implemented by command communication. In this embodiment, since the signal path is used for the handshake operation at the time of irradiation and the dose control of the radiation, the signal path is arranged to transmit the radiation irradiation stop control signal in, for example, several ms. From this viewpoint, for example, a photocoupler, a photo-MOS relay, or the like can be used as a device used in a signal processing unit. For example, a communication method using wired 100BaseTX/1000BaseT which can ensure the communication time and delay time can be used in the command communication. By ensuring the reliability and responsiveness, a signal path using wireless communication can also be used.

Next, a dose detection example in the radiation imaging apparatus 1001 will be described with reference to FIG. 10. 10a in FIG. 10 is a view exemplifying the positional relationship between an image at the time of chest imaging and lighting fields 1012 (lighting fields 1013 to 1017). In chest imaging, the dose of a region corresponding to a lung field portion 1019 indicated in gray in 10a of FIG. 10 is normally controlled. The operator selects to detect the radiation using two lighting fields, that is, the lighting fields 1015 and 1016 as the lighting fields corresponding to the lung field portion 1019. The detection area of the digital signal path (first signal path) is also set based on this selection result. The digital processing unit 401 in the radiation imaging apparatus 1001 can be arranged to calculate the irradiation dose and the dose information (integration dose) of the radiation based on output signals corresponding to the two lighting fields and output from the dose detection pixel 121. If the dose information (integration dose) of the output voltage from the dose detection pixel 121 and corresponding to at least one lighting field exceeds the threshold preset by the operator, the digital processing unit 401 changes the imaging preparation completion signal 902 from the preparation completion state to the preparation noncompletion state (noncompletion state) and outputs it even if the imaging preparation request signal 901 is set in the request state. That is, the digital processing unit 401 (first processing unit) outputs the stop signal (first stop signal) when the dose information obtained based on the first processing (digital signal processing) exceeds the threshold.

The signal (stop signal (first stop signal)) indicating the preparation noncompletion state (noncompletion state) is input to the signal processing unit 1045 via the relay unit 1023 and the signal processing unit 1024 of the imaging control apparatus 1002. When the imaging preparation request signal 901 is set in the request state, and the imaging preparation completion signal 902 is set in the noncompletion state, the signal processing unit 1045 outputs, to the signal selection unit 1043, a signal (stop signal (first stop signal)) representing the preparation noncompletion state (noncompletion state). Based on the signal representing the preparation noncompletion state (noncompletion state) input via the signal selection unit 1043, the radiation generation control unit 1042 controls the radiation source 1003 to stop irradiation of the radiation 1103 upon detecting that the imaging preparation completion signal 902 is changed to the preparation noncompletion state.

In 10b of FIG. 10, the detection area in the digital signal path is set as the lighting field 1017. In this example, the digital processing unit 401 (first processing unit) detects that the minimum dose in the region of interest reaches the dose satisfying the image quality and outputs a signal (stop signal (first stop signal)) indicating the preparation noncompletion state (noncompletion state). That is, when the dose information obtained based on the first processing (digital signal processing) exceeds the dose set as the threshold to satisfy the image quality of the region of interest, the digital processing unit 401 (first processing unit) outputs the signal (stop signal (first stop signal)) indicating the preparation noncompletion state (noncompletion state). The digital processing unit 401 (first processing unit) generates an image (reduced image) while performing digital signal processing of the output voltage output from the dose detection pixel 121 and corresponding to the lighting field 1017 and integrating the output voltage. If a minimum pixel value of the image (reduced image) generated while performing noise reduction processing is equal to or larger than the preset threshold, the digital processing unit 401 determines that the minimum dose in the region of interest reaches the dose satisfying the image quality. When the integration value of the output voltage output from the dose detection pixel 121 and corresponding to the lighting field 1017 reaches the dose satisfying the image quality, the digital processing unit 401 (first processing unit) changes the imaging preparation completion signal 902 from the preparation completion state to the preparation noncompletion state (noncompletion state) even if the imaging preparation request signal 901 is set in the request state and outputs the imaging preparation completion signal 902. That is, if the dose information obtained based on the first processing (digital signal processing) exceeds the threshold, the digital processing unit 401 (first processing unit) outputs the stop signal (first stop signal). As in 10a of FIG. 10, the signal (stop signal (first stop signal)) indicating the preparation noncompletion state (noncompletion state) is input to the signal processing unit 1045 via the relay unit 1023 and the signal processing unit 1024 of the imaging control apparatus 1002.

If the imaging preparation request signal 901 is set in the request state and the imaging preparation completion signal 902 is set in the noncompletion state, the signal processing unit 1045 outputs, to the signal selection unit 1043, the input imaging preparation completion signal 902 (noncompletion state) as the stop signal of the radiation 1103 in the digital signal path. When the radiation generation control unit 1042 detects that the imaging preparation completion signal 902 is changed to the preparation noncompletion state based on the signal representing the preparation noncompletion state (noncompletion state) and input to the signal selection unit 1043, the radiation generation control unit 1042 controls the radiation source 1003 to stop irradiation of the radiation 1103. The digital processing unit 401 (first processing unit) can set, as a pixel value serving as the threshold, for example, a value calculated based on a pixel value satisfying the SNR (Signal to Noise Ratio) of the image.

A case in which the method of 10b in FIG. 10 is useful will be described using 10c in FIG. 10. 10c in FIG. 10 is a view showing an example when a subject is small as compared to the imaging region. The area of the preset lighting field 1012 group is considerably shifted from a region corresponding to a lung field portion 1026 whose dose is actually controlled. In this example, low-dose areas which are not the lung field portion 1026 are considerably included in the lighting fields 1015 and 1016. In analog signal dose control, the threshold cannot be exceeded unless irradiation is performed with the radiation much exceeding the target dose of the lung field area. On the other hand, according to the dose control shown in 10b of FIG. 10 by which the digital processing unit 401 detects that the minimum dose in the lighting field 1017 reaches the dose satisfying the image quality, a low-dose arrangement can be implemented while satisfying good image quality suppressing excessive irradiation even in the case shown in 10c of FIG. 10.

Note that a region 1025 outside the irradiation area or a metal region (not shown) in a body is an area in which sufficient radiation does not reach and the radiation need not be reached. If this region enters the area of the lighting field 1017 to detect the minimum dose, dose suppression cannot be performed by the minimum dose detection method described in 10b of FIG. 10. For this reason, the radiation imaging system 1000 according to this embodiment can set the region of interest corresponding to the lighting field 1017 based on imaging portion information based on an instruction from the operator and irradiation area information from the radiation generation control unit 1042. Also, as for the region 1025 outside the irradiation area or the metal portion (not shown) in the body, the radiation imaging system 1000 according to this embodiment can calculate an appropriate minimum dose by presetting from past images, setting of a divided region at the time of generating an image (reduced image) to be large with respect to a metal and preforming median filtering, or performing image processing for excluding a geometric region from arithmetic operation in real time.

According to the present invention, control can be performed so as to stop the radiation irradiation using a plurality of kinds of signals. By radiation irradiation stop control using the plurality of kinds of signals, excessive irradiation can be suppressed, and an arrangement with a low dose can be implemented.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. A radiation imaging system, comprising:
a detection unit configured to include a conversion element for converting radiation irradiation from a radiation source into a signal and to detect the radiation;
a first processing unit configured to output a first stop signal when dose information of the radiation obtained based on first processing for the signal converted by the conversion element exceeds a threshold;
a second processing unit configured to output a second stop signal when dose information of the radiation obtained based on second processing on a signal having undergone the first processing exceeds a threshold; and
a control unit configured to control the radiation source so as to stop the radiation irradiation based on the first stop signal or the second stop signal.
2. The radiation imaging system according to claim 1, wherein the second processing unit comprises a conversion processing unit configured to output a signal having undergone the second processing to a signal having undergone the first processing by the first processing unit; and
an integration determination unit configured to determine whether dose information obtained by performing integration on a signal output from the conversion processing unit exceeds a threshold.

3. The radiation imaging system according to claim 2, further comprising a communication unit configured to output a signal output from the first processing unit via a first signal path, and to output a signal output from the conversion processing unit via a second signal path.

4. The radiation imaging system according to claim 2, wherein the second processing unit outputs the second stop signal if the integration determination unit determines that the dose information exceeds the threshold.

5. The radiation imaging system according to claim 1, further comprising a selection unit configured to select the first stop signal or the second stop signal, wherein
the selection unit selects a signal first input to the selection unit, out of the first stop signal and the second stop signal.

6. The radiation imaging system according to claim 5, wherein the control unit controls the radiation source so as to stop irradiation of the radiation based on a signal selected by the selecting unit.

7. The radiation imaging system according to claim 1, wherein the first processing unit generates, as the first processing, a signal obtained by performing digital signal processing on the signal converted by the conversion element.

8. The radiation imaging system according to claim 7, wherein the first processing unit outputs the generated signal as a synchronization control signal with the radiation source.

9. The radiation imaging system according to claim 2, wherein the conversion processing unit generates, as the second processing, a signal obtained by performing analog conversion processing on a signal generated by the first processing unit.

10. The radiation imaging system according to claim 1, further comprising a setting unit configured to set an irradiation area of the radiation source; and
an identifying unit configured to identify a detection unit arrayed at a position corresponding to the set irradiation area, out of a plurality of detection units arranged in an imaging region.

11. The radiation imaging system according to claim 10, further comprising an obtaining unit configured to obtain information of an imaging portion of a subject, wherein
the identifying unit identifies a detection unit arrayed at a position corresponding to an imaging portion of the subject, out of a plurality of detection units arrayed in the imaging region.

12. The radiation imaging system according to claim 10, wherein the first processing unit obtains the dose information based on a detection result of the identified detection unit.

13. The radiation imaging system according to claim 1, wherein the first processing unit outputs a first stop signal when dose information obtained based on the first processing exceeds a dose set to satisfy image quality as the threshold in a region of interest.

14. A radiation imaging apparatus, comprising:
a detection unit configured to include a conversion element for converting radiation irradiation from a radiation source into a signal and to detect the radiation; and
a signal processing unit including a processing unit configured to output a stop signal when dose information of the radiation obtained based on first processing for the signal converted by the conversion element exceeds a threshold and a conversion processing unit configured to output a signal obtained by performing second processing on a signal having undergone the first processing by the processing unit.

15. The radiation imaging apparatus according to claim 14, wherein the processing unit generates, as the first processing, a signal obtained by performing digital signal processing on the signal converted by the conversion element.

16. The radiation imaging apparatus according to claim 14, wherein the conversion processing unit generates, as the second processing, a signal obtained by performing analog conversion processing on a signal generated by the processing unit.

17. The radiation imaging apparatus according to claim 14, further comprising a communication unit configured to output a signal output from the processing unit via a first signal path, and to output a signal output from the conversion processing unit via a second signal path.

18. A radiation imaging method, comprising the steps of:
a step of causing a detection unit that includes a conversion element for converting radiation irradiation from a radiation source into a signal, to detect the radiation;
a step of outputting a first stop signal when dose information of the radiation obtained based on first processing for the signal converted by the conversion element exceeds a threshold;
a step of outputting a second stop signal when dose information of the radiation obtained based on second processing for a signal having undergone the first processing exceeds a threshold; and
a step of controlling the radiation source so as to stop irradiation of the radiation based on the first stop signal or the second stop signal.

19. A computer-readable storage medium storing a program for causing a computer to execute each step in a radiation imaging method, the method comprising:
a step of causing a detection unit that includes a conversion element for converting radiation irradiation from a radiation source into a signal, to detect the radiation;
a step of outputting a first stop signal when dose information of the radiation obtained based on first processing for the signal converted by the conversion element exceeds a threshold;
a step of outputting a second stop signal when dose information of the radiation obtained based on second processing for a signal having undergone the first processing exceeds a threshold; and
a step of controlling the radiation source so as to stop irradiation of the radiation based on the first stop signal or the second stop signal.

* * * * *